United States Patent [19]

Joyce et al.

[11] Patent Number: 5,168,044

[45] Date of Patent: Dec. 1, 1992

[54] IMMUNODIAGNOSTIC ASSAYS FOR USE IN THE DETECTION AND DETERMINATION OF MASTITIS

[75] Inventors: Patrick J. Joyce, Blackrock; Catherine A. O'Sullivan, Bray; Alan G. Shattock, Blessington; Teresa M. Sloan, Dundalk, all of Ireland

[73] Assignee: University College Dublin, Belfield, Ireland

[21] Appl. No.: 453,811

[22] Filed: Dec. 20, 1989

[30] Foreign Application Priority Data

Dec. 22, 1988 [IE] Ireland ............................. 3863/88

[51] Int. Cl.⁵ ................... G01N 33/53; G01N 33/577
[52] U.S. Cl. ................... 435/7.24; 435/7.5; 435/7.9; 435/7.92; 435/961; 436/534; 436/174; 436/63; 436/548
[58] Field of Search .............. 435/7.24, 7.9, 7.94, 435/7.95, 172.2, 240.27, 975, 961.75; 436/548, 534, 518, 174; 530/387

[56] References Cited

FOREIGN PATENT DOCUMENTS 36496 11/1974 Israel .

OTHER PUBLICATIONS

Nickerson et al, "Production of Monoclonal Antibodies to Bovine Leukocyte Cell-Surface Components" Journal of Dairy Science, 66(7) pp. 1547-1558 (1983).

Lostrie-Trussart et al, "Phagocytic Cells of Cow's Milk: Identification with Monoclonal Antibodies and Functional Study in vitro", Annales de Medecine Veterinaire, 131(1) pp. 49-62 (1987).

Sevier et al, "Monoclonal Antibodies in Clinical/Immunology", Clin. Chem 27(11) pp. 1797-1806 (1981).

Ball et al., J. Clin. Microbiol., 29(8):1625-1628 (Aug. 1991).

International Dairy Federation Annual Bulletin, "A Monograph on Bovine Mastitis-Part I" pp. 3-5 (1971).

Darnell et al, eds., Molecular Cell Biology pp. 157 and 166.

Aldrich Chemical Company, Inc. catalog p. 355 (1990).

Primary Examiner—Esther L. Kepplinger
Assistant Examiner—Carol E. Bidwell
Attorney, Agent, or Firm—Felfe & Lynch

[57] ABSTRACT

Immunodiagnostic assays for the detection and determination of mastitis and sub-chemical mastitis comprise capturing neutrophils or fragments or soluble products thereof in a milk sample on an insolubilized form of a corresponding antibody, optionally using conditions whereby the cells in the milk sample are lysed. Monoclonal antibodies are provided which can be used in said assays and which are specific to neutrophils.

10 Claims, 1 Drawing Sheet

IMMUNODIAGNOSTIC ASSAYS FOR USE IN THE DETECTION AND DETERMINATION OF MASTITIS

FIELD OF THE INVENTION

This invention relates to immunodiagnostic assays for the detection and determination of mastitis and sub-clinical mastitis and to monoclonal antibodies for use in said assays.

BACKGROUND AND PRIOR ART

Mastitis can be defined as inflammation of the mammary glands and is caused by a variety of microbial infections. Ordinarily, but not necessarily, bovine mastitis reflects the presence of pathogenic bacteria in the milk compartment of the udder. Two of the commonest bacteria associated with this disease are *Staphylococcus aureus* and *Streptococcus agalactiae* which are contagious and live on or in the cow's udder. Other species of bacteria involved in the disease are found in the environment of the cows.

Bovine mastitis causes more financial loss to the dairy industry than any other disease. Approximately 70% of this loss is attributed to reduced milk production caused by sub-clinical mastitis, which dairy producers seldom recognize. In addition to the loss of milk production, manufacturers of dairy products also lose money because of the adverse processing qualities of mastitic milk due to compositional changes. The major effect of the altered milk composition, particularly the lower caesin and fat levels, is a lower cheese yield.

There are several tests in use to detect mastitis infections, including milk somatic cell counts and tests based on various compositional changes in the milk. The use of somatic cell counts to diagnose udder disease was the first widely used screening procedure, and even today has retained its position as the most reliable and specific test for mastitis diagnosis. Increased levels of somatic cells can be detected by a variety of direct and indirect methods. As milk somatic cell numbers can be influenced by factors other than inflammation, for example, stage of lactation, number of lactations, stress, nutritional problems, etc., such tests are not very specific. Furthermore, this type of testing is cumbersome, in many cases expensive and not suitable for use at the cow-side.

One of the most dramatic changes seen in mastitic milk over normal milk is the ratio of lymphocytes:neutrophils:epithelial cells. In normal milk this ratio is 1:1.5:14. In mastitic milk this ratio is significantly raised, for example, 1:10:10. This increase in neutrophils is apparently specific for mastitis, and a rapid immunodiagnostic test for the quantitation of bovine neutrophils in milk would be of considerable benefit in the diagnosis and control of this condition. Furthermore, due to E.E.C. directives, in 1989 milk with 500,000 somatic cells per ml will not be acceptable and in 1990 this number will be 400,000. A specific test which would quantify neutrophils would indicate to the farmer animals with sub-clinical mastitis. Such animals could be treated with appropriate antibiotics which would circumvent milk losses.

Monoclonal antibodies have been developed to neutrophils in bovine blood and have been used to identify subpopulations therein (M. J. Paape et al. Journal of Diary Science, Vol. 71, Supplement 1, 1988 p. 258). A monoclonal antibody has also been developed to identify bovine neutrophils in milk (Lostrie-Trussart et al; Annales de Medicine Vetinaire, Vol. 131, No. 1, 1987, p. 49). A further series of monoclonal antibodies to bovine neutrophils, not thoroughly characterised have been produced, and were proposed as a means of examining the nature and number of antibody binding sites on neutrophils of bovine blood and milk as a method of distinguishing between these cells, and for use in identification of neutrophil subpopulations important to mastitis resistance (Nickerson et al. Journal of Dairy Science, Vol. 66, No. 7, 1983, p. 1547). However, none of these three references describes or proposes the use of such monoclonal antibodies in a diagnostic assay for mastitis. This is not unexpected because it has not heretofore been appreciated that neutrophil-like cells are the important cells to monitor in mastitis. It has now been found and as hereinafter demonstrated that when a milk sample has greater than 250,000 somatic cells/ml, the cells in excess of 250,000 are almost entirely made up of neutrophils It is an object of the present invention to provide an assay for the detection of mastitis, including sub-clinical mastitis, caused by any aetiologic agent, which overcomes the aforementioned disadvantages and which can be readily carried out by farmers and veterinarians in addition to laboratory personnel.

SUMMARY OF THE INVENTION

Immunodiagnostic assays are provided for the detection and determination of mastitis and sub-clinical mastitis which comprise capturing neutrophils or fragments or soluble products thereof in a milk sample on an insolubilized form of a corresponding antibody, optionally using conditions whereby the cells in the milk sample are lysed. Monoclonal antibodies are provided which can be used in said assays and which are specific to neutrophils.

DETAILED DESCRIPTION OF PREFERRED EMBODIMENTS

According to one aspect of the invention there is provided a monoclonal antibody for use in an immunoassay method for detecting or determining mastitis which a) reacts with neutrophils or fragments or soluble products thereof, but b) does not react with any of the other types of cells found in milk or fragments or soluble products thereof.

The monoclonal antibody may suitably be human, mouse or rat monoclonal antibody prepared by conventional methods, including those methods currently available for producing monoclonal antibodies on a commercial scale, genetically engineered monoclonal antibody or antibodies fragments or antibody produced by in vitro immunization with certain cells.

Preferably the monoclonal antibody is of class IgG.

The monoclonal antibody in accordance with the invention may be produced by a hybridoma formed by fusion of spleen cells from a human, mouse or rat previously immunized with neutrophils or fragments or soluble products thereof and cells from a myeloma line selected from human, mouse and rat myeloma lines.

The monoclonal antibody is suitably one which reacts with bovine neutrophils or fragments or soluble products thereof. Such a monoclonal antibody is preferably produced by a hybridoma as herein defined.

However, it will be appreciated that monoclonal antibody could also be produced from a suitable Fab fragment coded by a DNA sequence in accordance with the method of Skerra, A. and Plückthun, A. (1988); Science 240, 1038-1041 or by the polymerase chain reaction (PCR) technique according to the method of Orlandi, R. et al.; Proc. Natl. Acad. Sci. U.S.A. 86, 3833-3837.

The monoclonal antibody preferably reacts with a heat labile protein material which is specific to neutrophils and has a molecular weight in the range of from 10,000 to 20,000 daltons, more especially 12,000-16,000 daltons.

A particularly preferred monoclonal antibody in accordance with the invention is that obtained from the hybridoma of clone 3G5 U.C.D. hereinafter described in Examples 1 and 3. A sample of the hybridoma known as 3G5 U.C.D. was deposited at the European Collection of Animal cell Cultures (ECACC), Porton Down, Salisbury, Wiltshire, SP4 OJG United Kingdom on Sep. 5, 1989 and accorded the Cell Deposit No. 89090501 in accordance with the Budapest Convention. As hereinafter demonstrated clone 3G5 U.C.D. produces monoclonal IgG antibody specific for bovine neutrophils or fragments or soluble products thereof, but does not react significantly with other types of cells found in bovine milk, viz. T lymphocytes, B lymphocytes and epithelial cells.

The invention also provides a cell line which produces a monoclonal antibody as hereinbefore specified.

Mammalian monoclonal antibody according to the invention may be prepared by a method which comprises:
i) immunizing the mammal with neutrophils or fragments or soluble products thereof;
ii) removing the spleen from said mammal and making a suspension of spleen cells;
iii) fusing said spleen cells with appropriate mammalian myeloma cells;
iv) screening the resultant hybridomas in separate wells in a medium which will not support the unfused myeloma cells for those with supernatants containing antibody which gives selective binding to neutrophils or fragments or soluble products thereof;
v) selecting and cloning hybridomas producing the desired antibody; and
vi)a) recovering the antibody from the supernatant above said clones, or, alternatively,
vi)b) transferring said clones intraperitoneally into a mammal and harvesting the malignant ascites from said mammal.

In either of the above two methods the mammals are suitably immunised with bovine neutrophils or fragments or soluble products thereof.

In relation to the above methods the animal systems used may be, for example, human-human, mouse-mouse, rat-mouse and rat-rat. An obvious exception would be any method involving the transfer of clones intraperitoneally into a human and harvesting malignant ascites or other procedure which would be considered unethical in the case of humans.

The invention also provides an immunoassay method for detecting or determining mastitis or sub-clinical mastitis, which method comprises capturing neutrophils or fragments or soluble products thereof from a milk sample, wing an antibody, such as insolubilised form of a corresponding antibody and confirming the presence of the neutrophils or fragments or soluble products thereof bound to said insolubilised antibody.

Whole neutrophils can be captured by a solid phase antibody in accordance with the above method according to the invention, however, the neutrophils are susceptible to being knocked off the solid phase by the washing steps which will normally form part of the method.

The soluble neutrophil products detected by monoclonal and polyclonal antibody in accordance with the invention are freely excreted in mastitic milk and it is likely such soluble products represent breakdown products of the neutrophil. The amount of this breakdown product may vary, making quantitation somewhat difficult. Furthermore, antibodies, such as IgA antibody and other proteins may bind the epitopes concerned.

Accordingly, the invention provides an immunoassay method for detecting or determining neutrophils in milk, which method comprises subjecting a milk sample to lysis so as to lyse neutrophils, capturing neutrophil fragments or soluble products thereof by means of an insolubilized form of a corresponding antibody and measuring the presence of the neutrophil fragments or soluble products thereof in the sample by determining the bound neutrophil fragments or soluble products thereof.

The milk sample may be lysed in various ways. For example, the cells of the milk sample may be lysed by first freezing the milk sample and then thawing said sample. Other lysis techniques such as ultra-sonication may also be used.

Lysis may also be achieved with various lysing agents including high or low concentrations of suitable salts, surfactants, especially detergents, enzymes, complement and complement fixing antibody and various dissociating agents.

Most of the above lysing systems do not interfere with the capture of the neutrophil fragments or soluble products of neutrophils by monoclonal or polyclonal antibody so that the lysis reaction can take place in situ as part of the particular test being carried out.

Surfactants for use as a lysing agent in accordance with the invention may be selected from any suitable anionic, cationic or non-ionic surfactant.

Suitable surfactants include polyoxyethylene esters of fatty acids, polyoxyethylene sorbitan esters, polyoxyethylene alcohols, polyoxyethylene isoalcohols, polyoxyethylene esters, polyoxyethylene-p-t-octylphenols or octylphenyl-ethylene oxide condensates, ethylene oxide condensates with fatty alcohols, polyoxyethylene nonylphenols, sodium N-lauroylsarcosinate, sodium dodecyl N-sarcosinate, sodium dodecyl sulphate, cetyltrimethylammonium bromide, dodecyl pyridinium chloride, palmitoyl lysolecithin, dodecyl-N-betaine, sodium dodecyl sulphate, tetradecyl ammonium bromide and saponin or a mixture thereof.

Non-ionic surfactants are especially preferred. Such preferred non-ionic surfactants being:
polyoxyethylene sorbitan esters sold under the Trade Mark TWEEN, especially polyoxyethylene sorbitan monolaurate or TWEEN 20, but also TWEEN 60 and TWEEN 80;
polyoxyethylene ethers sold under the Trade Mark TRITON, such as TRITON X100, TRITON X114, TRITON X110E and TRITON N101, and BRIJ;

an octylphenyl-ethylene oxide condensate sold under the Trade Mark NONIDET P40; and ethylene oxide condensates of fatty alcohols sold under the Trade Mark LUBROL, especially LUBROL PX.

Suitable dissociating agents for use as a lysing agent in accordance with the invention are selected from thiocyanates, hydrochlorides, bromides, chlorides, sulphates and ureas and especially the sodium, potassium, ammonium and guanidine salts thereof.

Especially suitable dissociating agents are selected from potassium thiocyanate, sodium thiocyanate, guanidine thiocyanate, guanidine hydrochloride, potassium iodide, ammonium chloride, ammonium sulphate and urea or a mixture thereof.

Whereas surfactants or dissociating agents alone can be used as the lysing agent in accordance with the invention, it is found the use of a combination of a surfactant and a dissociating agent exhibits a synergistic effect.

Where the lysing agent comprises a combination of a surfactant and a dissociating agent, the surfactant and the dissociating agent are preferably selected from those specifically hereinbefore mentioned.

The invention also provides a method for detecting or determining neutrophils in milk, which method comprises coating a surface with neutrophils or fragments or soluble products thereof or lysed cell material prepared by a method hereinbefore specified, adding an amount of an antibody to neutrophils or fragments or soluble products thereof, allowing the immunochemical reaction to take place and estimating the amount of antibody bound to the neutrophil, neutrophil fragment or soluble product thereof.

Antibody for use in the methods according to the invention is preferably a monoclonal antibody as hereinbefore described. Such antibody may be derived from the supernatants of a hybridoma or myeloma as hereinbefore defined and prepared or may be derived from malignant ascites in accordance with the method hereinbefore specified. Alternatively, and more usually, the monoclonal antibody will be produced by currently available methods for producing bulk monoclonal antibody or by genetic engineering.

Alternatively, the antibody for use in any one of the immunoassay methods hereinbefore specified may be polyclonal antisera as previously indicated.

The immunoassay methods in accordance with the invention may be carried out using any known format, such as, for example, plates, particles, strips, beads, rods, dipsticks, membranes, etc.

For example, insolubilized or solid phase antibody as used herein is suitably bound to a dipstick, particle, plate, well, membrane, tube, bead, rod or the like of plastics material or glass in a manner known per se. Beads of latex, nylon or other suitable material may also be used, as may liposomes, according to methods known per se.

More specifically, the insolubilised form of the antibody comprises said antibody adsorbed on a surface adapted for protein adsorption. Said surface may be a particle, plate, well, membrane, tube, bead, rod, liposome or the like and of a material as hereinbefore specified.

Under laboratory conditions suitably the surface comprises a plastics microtitration plate or strip adapted for protein adsorption wherein the immunochemical reaction and the estimation of the antigen can take place, following capturing of the antigen or release of the antigen on the insolubilised form of the antibody, depending on the method used. Especially suitable microtitration plates are gamma-irradiated microtitration plates. Examples of such gamma-irradiated microtitration plates are flat-well polystyrene microtitration plates marketed by DYNATECH under the Trade Mark MICROELISA and those sold under the Trade Mark "NUNC" IMMULON. Examples of strips are strips marketed by DYNATECH under the Trade Mark REMOVAWELL.

The relevant surface may be coated directly with an optimum dilution of polyclonal antibody prepared by separating the relevant immunoglobulin fraction of antiserum or, alternatively, monoclonal antibody in accordance with the invention.

The estimation of the bound antigen derived from the sample can be carried out by enzymatic, fluorometric, luminometric or radiometric assay, using enzymes, fluorochromes, light-emitting probes or radio labels, respectively. In qualitative and semi-quantitative assays the estimation may be carried out visually, for example, when the assay involves the use of colored beads or the like as herein described.

The labelled agents for use in the assays according to the invention are prepared in conventional manner, as described hereinafter in the Examples, or are purchased from appropriate suppliers. Such labelled agents are normally in the form of conjugates such as enzyme-labelled antibodies for use in competitive binding assays. The labelled agent is also suitably an antibody covalently linked to a radio label for use in a radiometric assay, when the assays are carried out under laboratory conditions. The radio label is preferably $^{125}I$.

Under laboratory conditions the estimation of the bound antigen is preferably carried out by enzyme immunoassay using a suitable peroxidase labelled antibody or other suitable peroxidase conjugate. A suitable peroxidase is horseradish peroxidase. One such other suitable peroxidase conjugate is an avidin-biotin peroxidase complex, which may be used with an antibody biotin conjugate to amplify the enzyme assay in conventional manner. In such an enzyme assay antigen insolubilized on solid phase antibody binds to the antibody-biotin complex which in turn binds to the avidin/streptavidin-biotin peroxidase complex, whereupon the peroxidase activity is measured.

The immunoassay methods according to the invention may also involve the use of coloured beads or a coloured material or dye encapsulated in liposomes or other particles, said beads, liposomes or particles having an antibody bound thereto and being adapted to move relative to and come in contact with a further insolubilised antibody on a support member when a milk sample containing said antigen comes in contact with said beads, liposomes or particles. The methodology used in such an assay is described for example in EP-A-0 154 749 (Becton Dickinson and Company). Such a system is particularly suited for use as a cowside test or for use by veterinarians in the field because of the ease of use of such a system and the visual indication of a positive result, as further described in Example 10. A system of this type, which is a one-step assay procedure, can also be used as a semi-quantitative test if one uses a series of barriers, each comprising a predetermined quantity of said further insolubilized antibody in spaced apart relationship along said support member and such that said beads move progressively along said support member until all of the binding sites on said further insolubilised antibody defining said barriers are occupied, thereby providing an indication of the amount of said antigen in said sample. The further antibody may be identical to that bound on the beads, liposomes or particles or antibody to said bound antibody.

The invention also provides various test kits or packs containing the necessary components/ingredients for carrying out the methods according to the invention. Such a test kit or pack may include antibody coated tubes containing all of the necessary components for carrying out the methods according to the invention when a sample of milk is added thereto. Alternatively, one may provide a tube containing a lysis buffer reagent and an antibody-enzyme conjugate to which one adds a sample of milk, which tube is used with an antibody-coated dipstick for a competitive enzyme immunoassay.

A strip containing all of the necessary components/ingredients for carrying out a rapid, one-step assay in accordance with the invention when a milk sample is applied thereto is described above and is further illustrated in Example 10.

The present invention provides methods for the qualitative, quantitative or semi-quantitative detection of neutrophils or fragments or soluble products thereof, using immunoassays with monoclonal antibody as hereinbefore described or polyclonal antibody. The methods in accordance with the invention are capable of distinguishing between milk samples from normal healthy animals, mastitic animals and most importantly from animals with sub-clinical mastitis. Thus the milk of such animals can be prevented from contaminating bulk milk and the animals can be treated before the infection has gone too far. Since infection would be detected earlier, shorter lasting antibiotics may be usable for treatment thus allowing the animal back to useful milk production earlier. Antibiotic residues in milk are forbidden in many countries.

The invention will be further illustrated by the following Examples.

EXAMPLE 1

Monoclonal Antibody Production

Monoclonal Antibody No. 3G5 U.C.D. referred to above and specific for bovine neutrophil, was developed as follows:

Neutrophils for immunizations and screening were isolated from peripheral blood of cows by the method of Carlson G. P. and Kaneko J. J. 1973, PSEBM, Vol. 142, p. 853–856.

Lysed cell material was prepared using a lysis buffer consisting of 0.155M ammonium chloride, 0.001M potassium hydrogen carbonate and 0.00013M monosodium EDTA, pH 7.3, followed by freezing at $-20°$ C.

A six week old BALB/c mouse was immunized intraperitoneally (ip) with $10^7$ bovine neutrophil cells in phosphate buffered saline (PBS) followed six weeks later by three ip injections of 35 $\mu$g of lysed neutrophil material in incomplete Freund's adjuvant at ten day intervals. Three days after a final ip boost of 35 $\mu$g of lysed neutrophil material in incomplete Freund's adjuvant, the spleen was harvested.

Fusion of the mouse spleen cells with SP2/O murine myeloma cells was carried out by standard procedures (Kohler G and Milstein C, 1975. Nature, Vol. 256, p 495).

Hybridomas containing antibodies reactive with lysed bovine neutrophils were selected and cloned by limiting dilution in the presence of spleen feeder cells three times.

Clone 3G5 U.C.D. contains monoclonal IgG antibody specific for bovine neutrophil fragments and soluble products thereof and does not react significantly with other types of cell and epithelial cells. The following Examples illustrate these properties and their usefulness in tests for mastitis.

EXAMPLE 2

Indirect ELISA on lysed bovine neutrophils and lysed bovine lymphocyte antigens 50 ng of lysed cell material prepared according to the procedure of Example 1 was coated onto microtitre plates overnight at 4° C. as the solid phase. The plates were washed three times in PBS containing 0.05% TWEEN 20 (PBST) and quenched with PBS containing 0.3% TWEEN 20 for 1 h. at room temperature. 100 $\mu$l of hybridoma or SP2/O myeloma supernatants was added to each well for 1.5 h. at room temperature. The plates were washed five times with PBST. 100 $\mu$l of rabbit anti-mouse Ig conjugated to horse-radish peroxidase (HRPO) (Dako), which had been previously incubated with 3% normal human serum for 30 min., was added at a dilution of 1/500 for 1.5 h. at room temperature. The plates were washed seven times with PBST and o phenylene diamine (OPD) chromogen containing 0.3% hydrogen peroxide in citrate phosphate buffer pH 5.5 was added to each well (100 $\mu$l) for 30 min.. The reaction was stopped with 5N $H_2 SO_4$ (50 $\mu$l) and the plates were read at 492 nm.

The results are depicted in Table 1.

TABLE 1

| Solid Phase: | O.D. 492 nm Lysed Neutrophils | O.D. 492 nm Lysed Lymphocytes* |
| --- | --- | --- |
| 3G5 U.C.D. MAB neat | >2.00 | 0.31 |
| 3G5 U.C.D. MAB 3:1 with PBS | 1.80 | 0.27 |
| 3G5 U.C.D. MAB 1:1 with PBS | 1.35 | 0.24 |

*Lymphocyte preparations are probably contaminated with some neutrophils.

The above results indicate a good degree of specificity of the 3G5 U.C.D. monoclonal antibody for bovine neutrophils.

EXAMPLE 3

Characterisation and Sensitivity of 3G5 U.C.D. Monoclonal Antibody

The molecular weight of the target neutrophil protein was determined by means of the Western Blot technique, using purified bovine neutrophil and lymphocyte proteins prepared by conventional SDS PAGE (Sodium Dodecyl Sulphate PolyAcrylamide Gel Electrophoresis) on a 12.5% acrylamide gel. The 3G5 U.C.D. monoclonal antibody reacted strongly only with an approximately 14,000 dalton protein from the purified neutrophil preparation as prepared in Example 1. as detected by HRPO labelled anti-mouse Ig using 4-chloronaphthol as substrate.

The monoclonal antibody 3G5 U.C.D. was isotyped by immunodiffusion using a CN Immunobiologicals Mouse Monoclonal Typing Kit, Cat. No. C46901, and was typed as IgG, subclass IgG1.

An experiment was carried out which demonstrated that 3G5 U.C.D. monoclonal antibody (MAB) reacts only with neutrophils and probably only with a membrane component thereof:

Paramagnetic tosylated DYNABEADS M280, (DYNABEADS is a Trade Mark—Dynal Ltd., Liverpool) were coated with rabbit antimouse (Dako) and with 3G5 U.C.D. MAB from tissue culture fluid according to the manufacturer's instructions.

3 ml of fresh moderately mastitic milk were mixed with 7.5 μl of coated DYNABEADS and 3 ml of the same milk was mixed with 7.5 μl of rabbit anti-mouse Ig M280 DYNABEADS not coated with 3G5 U.C.D. MAB as a control. 1 ml of 60 h. old mastitic milk containing many lysed or degraded cells was also mixed with 5 μl of MAB 3G5 coated beads.

The mixtures thus formed were incubated with gentle rocking at 4° C. for 1 h. and then the bound cells were 'pulled' (removed) from the suspension by means of a strong magnet and then rinsed twice in PBS. A plain preparation of centrifuged cell pellet was also prepared.

Each of the preparations was smeared onto microscope slides, fixed by drying or glutaraldehyde and stained with DIFFQUICK (DIFFQUICK is a Trade Mark of Marz and Dade AG). A second set of slides was subjected to differential esterase counter-staining to distinguish neutrophils from lymphocytes.

The results obtained showed:
a) the great majority of cells pulled out of the mastitic milk by the 3G5 MAB coated beads were neutrophil polymorphonuclear granulocytes;
b) few cells were found in the uncoated bead preparation of the same mastitic milk;
c) there were very few cells from the mastitic sample not in contact with the coated beads; and
d) there were many large clumps of beads with cell debris and amorphous stained protein from the sample of 60 h. old milk.

Treatment of neutrophil antigen, prepared from purified bovine blood neutrophils and coated onto a solid-phase, with trypsin or pronase reduced the O.D. from an initial value of 1.87 to 0.44 and 0.23, respectively showing the antigen to be predominantly protein. The antigen was also found to be heat-labile, the O.D. being reduced from an initial value of 1.77 at 20° C. to 0.81 after 20 min. at 60° C., which is also evidence for the antigen being a protein.

Accordingly, the experiment indicates that 3G5 U.C.D. MAB reacts with a heat-labile, approximately 14,000 dalton M.W. protein which is abundant and specific to neutrophil granulocytes.

EXAMPLE 4

Indirect ELISA on Milk Samples

100 μl milk samples, to which was added either 100 μl of detergent, lysis buffer (as prepared in Example 7), distilled water or PBS, as specified in Table 2 below, were coated onto microtitre plates for two h. at room temperature. The plates were washed two to seven times with PBST and blocked with 0.3% TWEEN 20 in PBS for one h. at room temperature. 100 μl of 3G5 U.C.D. monoclonal antibody or myeloma supernatant (SP$_2$/O control) was added to each well for 1.5 h. at 37° C. The plates were washed four to seven times in PBST. 100 μl of rabbit antimouse Ig conjugated to HRPO (Dako) which had been absorbed with 3% normal human serum for 30 min., was added at a dilution of 1/500 for 1.5 h. at 37° C. The plates were again washed four to seven times with PBST. OPD substrate as used in Example 2 was added for ten to thirty min. at room temperature in the dark. The reaction was stopped with 50 μl of 5N H$_2$SO$_4$ and the plates were read at 492 nm.

TABLE 2

|  | O.D. AT 492 nm | |
|---|---|---|
|  | Normal Healthy Milk | Highly Mastitic Milk |
| 3G5 U.C.D. + Antigen | | |
| Milk Only | 0.065 | >2.0 |
| Milk + 1% NP40* | 0.290 | >2.0 |
| Milk + 10% NP40 | 0.150 | >2.0 |
| Milk + 1% T20** | 0.210 | >2.0 |
| Milk + 10% T20 | 0.160 | >2.0 |
| Milk + Lysis buffer | 0.050 | >2.0 |
| Milk + 1H$_2$O | 0.010 | >2.0 |
| Milk + PBS | 0.010 | >2.0 |
| CONTROLS: | | |
| SP$_2$/O supernatant + Antigen | | |
| Milk Only | 0.025 | 0.063 |
| Milk + 1% NP40 | 0.022 | 0.070 |
| Milk + 10% NP40 | 0.002 | 0.033 |
| Milk + 1% T20 | 0.040 | 0.020 |
| Milk + 10% T20 | 0.030 | 0.030 |
| Milk + Lysis buffer | 0.010 | 0.010 |
| Milk + 1H$_2$O | — | — |
| Milk + PBS | — | — |
| 3G5 U.C.D. − Antigen | | |
| Milk + substrate only | 0.000 | 0.00 |
| Milk + 3G5 U.C.D. + substrate only | 0.000 | 0.00 |
| Milk + SP$_2$/O + substrate only | 0.000 | 0.00 |
| Milk + 2nd antibody + substrate | 0.015 | 0.03 |

*Nonidet P40
**TWEEN 20

The above results clearly indicate that 3G5 U.C.D. MAB reacts with mastitic milk and not with normal healthy milk.

The results also show that the neutrophil product detected is present both in or on the cells and also is excreted or present as a natural breakdown product of neutrophils in the liquid phase of the milk.

Since normal milk contains lymphocytes and epithelial cells and some neutrophils, the absence of reactions with normal milks also shows the monoclonal antibody does NOT react significantly with these other cell types.

EXAMPLE 5

Indirect ELISA on cell pellets and supernatants from the normal, mastitic and intermediate milks Milk samples were centrifuged at 5,000 rpm for 15 min., three times in PBS. Pellets were vortexed vigorously in lysis buffer (prepared as in Example 1) prior to plating. The remaining steps of the indirect ELISA were carried out as described in Example 4. The results are shown in Table 3 and demonstrate that the antigen is "soluble" and is excreted into the milk supernatant.

TABLE 3

| Sample | 1st Antibody | O.D. 492 nm | −/− |
|---|---|---|---|
| SUPERNATANTS | | | |
| Mastitic milk | 3G5 U.C.D. | >2.000 | +++ |
|  | SP$_2$/O | 0.020 | — |
| Normal milk | 3G5 U.C.D. | 0.075 | — |

TABLE 3-continued

| Sample | 1st Antibody | O.D. 492 nm | +/− |
|---|---|---|---|
| | SP2/O | 0.011 | − |
| Intermediate 1 | 3G5 U.C.D. | 0.319 | + |
| | SP2/O | 0.075 | − |
| Intermediate 2 | 3G5 U.C.D. | 1.196 | ++ |
| | SP2/O | 0.035 | − |
| LYSED WASHED PELLETS | | | |
| Mastitic milk | 3G5 U.C.D. | >2.0 | +++ |
| | SP2/O | 0.34 | − |
| Normal milk | 3G5 U.C.D. | 0.115 | − |
| | SP2/O | 0.032 | − |
| Intermediate 1 | 3G5 U.C.D. | 0.430 | + |
| | SP2/O | 0.045 | − |
| Intermediate 2 | 3G5 U.C.D. | >2.0 | +++ |
| | SP2/O | 0.061 | − |

EXAMPLE 6

Indirect ELISA testing of 48 cattle from a dairy farm

The indirect enzyme immunoassay (EIA) test of Example 4 was carried out on 48 cattle from a dairy farm in County Wicklow, Ireland.

Samples from each of the four quarters were mixed for each cow. Quarters of each reactive cow were tested individually on samples taken the next day. The mastitic cows were unknown to the inventors until after the experiment.

The EIA test correctly identified four out of the forty-eight cows which either had clinical mastitis at the time of the test (one cow) or which had been treated for mastitis within the previous eight weeks (three cows).

EXAMPLE 7

CAPTURE EIA system for detecting mastitic milk

Solid phase wells are coated with 100 μl of neat tissue culture 3G5 U.C.D. supernatant or an optimum dilution of ascitic fluid purified in a manner known per se (such as sulphate precipitation or ion-exchange chromatography) overnight at 4° C. The coated solid phase is then washed twice with PBST and quenched by filling wells with 'normal' bovine non-mastitic milk (as determined by a total somatic cell count to only 6,000 cells/ml) for 1 h. at 37° C.

Polyclonal antibody for the conjugate is prepared by conventional innoculation procedures in a rabbit. The IgG fraction of this antibody is isolated and conjugated to HRPO by a modification of the method of Smith and Tedder, (J. Virol. Methods, 1981, 3, 1–11) without using dinitrofluorobenzene.

A lysis buffer is prepared by adding 3 ml of 6M potassium thiocyanate slowly to 6 ml of normal milk. 0.9 ml of TWEEN 20 is then added. The solution is rolled for 30 min. at room temperature and then filtered through a 0.22 μm ACRODISC (ACRODISC is a Trade Mark; Gelman) to remove particulate matter. Alternatively, samples are lysed by freezing at −20° C. and then thawing at 37° C.

Solid phase wells are washed three times with PBST. 50 μl test samples are added one to each well and one positive control mastitic sample and four negative control samples are included in each test run. 50 μl lysis buffer is added to each well and the wells are left to incubate for 1.5 h. at 37° C. Alternatively 100 μl of freeze-thawed milk is used. The wells are washed four times with PBST and then 150 μl conjugate diluted in PBST containing 40% normal milk and 10% ovalbumin is added to each well. The wells are then incubated for 1.5 h. in a water bath at 37° C. The wells are washed four times with PBST and 100 μl TMB or OPD substrate added for 30 min. at room temperature. The reaction is stopped with 50 μl of 5NH2SO4 and the samples read in a dual wavelength spectrophotometer at 450 nm (TMB) or 492 nm (OPD), reference 620 or 690 nm.

The cut-off of this laboratory test is defined according to common procedures such that cut-off=mean negative control+three standard deviations, determined from a minimum of 200 negative controls. These negative controls should be determined to contain, by conventional specific cell counting techniques, a ratio of milk neutrophils to lymphocytes of not more than 2:1 or have a total somatic cell count ≦6,000. The sensitivity of these assays can be adjusted by varying the concentration of solid phase antibody and/or conjugate.

By suitably adjusting the solid-phase and conjugate antibody concentrations it is possible to mix together sample, lysis buffer, solid phase antibody and conjugate simultaneously so that a quicker test results. Solid phase antibody and conjugate will bind to lysed cell breakdown product in a semi-competitive manner. To prevent saturation of neutrophils by conjugate the milk sample should be added to the well last or simultaneously with the solid phase.

EXAMPLE 8

Use of capture assay on milk samples from individual cattle and bulk tank from a dairy farm-field trial The capture assay described in Example 7 was used on milk samples from 23 cows and on milk samples from a bulk tank from a farm in County Wicklow, Ireland over a period of six weeks. The results are shown in Table 4. The somatic cell counts were carried out by Premier Dairies, Dublin.

TABLE 4

| TIME: OOW | Week 1 CC* EIA | Week 2 CC EIA | Week 3 CC EIA | Week 4 CC EIA | Week 5 CC EIA | Week 6 CC EIA | |
|---|---|---|---|---|---|---|---|
| 1 | 124 neg | 148 neg | 135 neg | 42 neg | 96 neg | 44 neg | |
| 2 | 100 neg | 71 neg | 42 neg | 40 neg | 389 neg | 397 +/− | |
| 3 | — | 1073 ++ | 710 + | 848 + | 703 + | 1014 ++ | Chronic positive |
| 4 | 548 + | 83 neg | 651 + | 104 neg | 43 neg | 76 neg | |
| 5 | 78 neg | 172 neg | 100 neg | 42 neg | 80 neg | 76 neg | ntb |
| 6 | 3140 +++ | 1912 ++ | 1665 ++ | 1226 ++ | 15722 ++ | 1949 ++ | |
| 7 | — | 131 neg | 304 neg | 1224 + | 248 neg | 297 neg | |
| 8 | 476 + | 152 neg | 107 neg | 32 neg | 69 neg | 109 neg | |
| 9 | 121 neg | 526 + | 128 neg | 153 neg | 321 neg | 268 neg | |
| 10 | 860 ++ | 659 + | 728 + | 878 + | 744 + | 697 + | ntb |
| 11 | 130 neg | 384 neg | 246 neg | 202 neg | 73 neg | 289 neg | |
| 12 | 31 neg | 122 neg | 46 neg | 70 neg | 115 neg | 49 neg | |
| 13 | 98 neg | 171 neg | 65 neg | 59 neg | 375 neg | 82 neg | |

TABLE 4-continued

| TIME: OOW | Week 1 CC* | Week 1 EIA | Week 2 CC | Week 2 EIA | Week 3 CC | Week 3 EIA | Week 4 CC | Week 4 EIA | Week 5 CC | Week 5 EIA | Week 6 CC | Week 6 EIA | |
|---|---|---|---|---|---|---|---|---|---|---|---|---|---|
| 14 | 62 | neg | 78 | neg | 50 | neg | 21 | neg | 67 | neg | 74 | neg | |
| 15 | 289 | neg | 460 | + | 391 | + | 186 | neg | **529 | neg | 235 | neg | |
| 16 | 373 | + | 674 | + | 605 | + | 1034 | + | 401 | neg | 679 | + | low 8–9 months earlier |
| 17 | — | | 127 | neg | 107 | neg | 75 | neg | 61 | neg | 72 | neg | |
| 18 | 97 | neg | 346 | neg | 45 | neg | 130 | neg | 59 | neg | 128 | neg | |
| 19 | — | | — | | 1175 | ++ | 914 | + | 1809 | + | — | | Chronic positive |
| 20 | 94 | neg | 247 | neg | 92 | neg | 101 | neg | 58 | neg | 81 | neg | |
| 21 | 82 | neg | 504 | + | 88 | neg | 118 | neg | 202 | neg | 366 | +/− | |
| 22 | 160 | neg | 256 | neg | 133 | neg | 154 | neg | 423 | neg | 441 | neg | |
| 23 | 74 | neg | 38 | neg | 115 | neg | 35 | neg | 102 | neg | 25 | neg | |
| BULK | 373 | .166 | 320 | .242 | 271 | .266 | 269 | .189 | 474 | .221 | 352 | .433 | |

KEY TO TABLE 4:
*CC = Somatic cell counts × 10³
+/− O.D. on the cut-off of the test
+ in the above tests is where the O.D. rises above the O.D. of 500,000 cells/ml on a titration curve.
++ is an O.D. approximately twice that of the + point.
= An O.D. not indicating neutrophils above 500,000 but is above the lower readings.
ntb = not tested before
** = this is the only discrepant result, i.e. where the EIA test was negative but the SCC was reported to be above 500,000 cells/ml.
In the case of the bulk tank measurements the results are indicated as exact O.D. readings.

EXAMPLE 9

Figure 1:
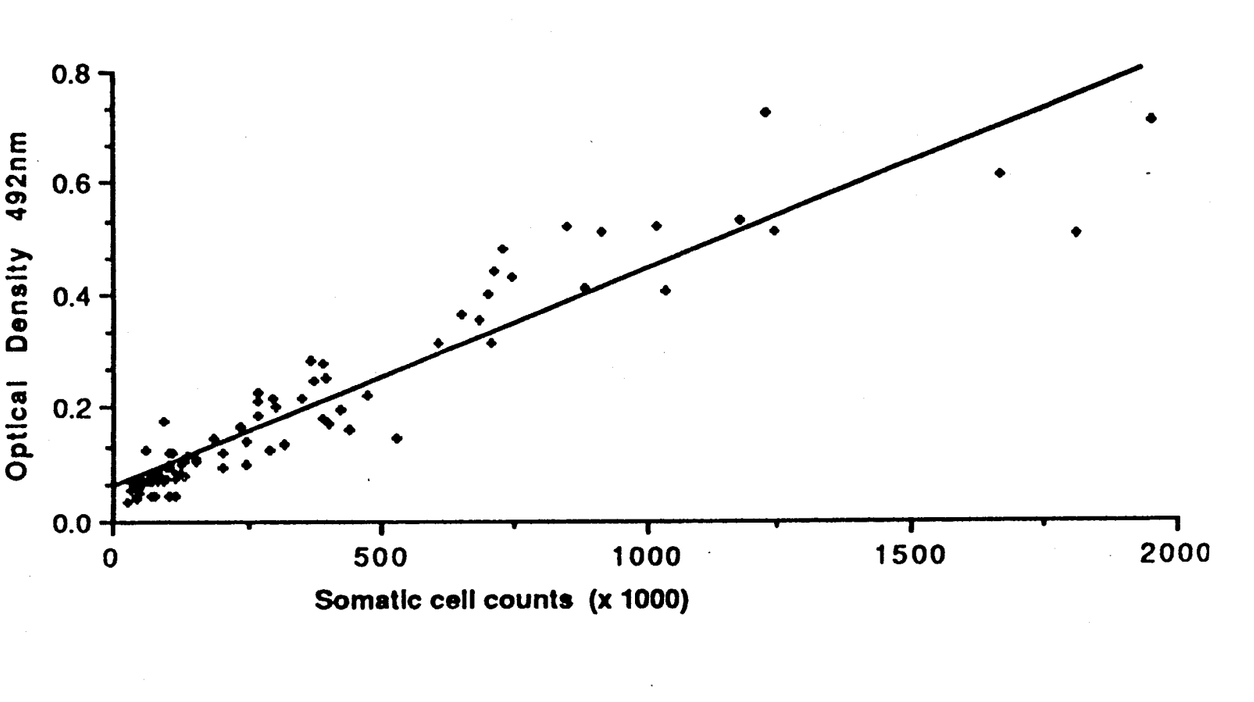
FIG. 1 is a graph of optical density versus somatic cell count in a capture assay in accordance with the invention as described in Examples 7 and 8.

Comparison of the sensitivity and specificity of the indirect ELISA versus capture assay on milk samples Experiments were carried out to determine the sensitivity and specificity of the indirect ELISA described in Example 4 versus the capture assay described in Example 7. Using the somatic cell count as the accepted standard with 500,000 cells as the cut-off for "positive", the following are the sensitivities and specificities calculated by plotting lines of "best fit" for the two assays:

|  | Sensitivity | Specificity |
|---|---|---|
| Indirect assay (188 samples) | 78.7% | 91.3% |
| Capture assay (95 samples) | 95.2% | 97.3% | from which it can be seen that the capture assay is more sensitive and much more specific than the indirect assay. The data from Example 8 are plotted in the accompanying graph.

EXAMPLE 10

Rapid one-step assay for the detection of mastitis or sub-clinical mastitis in cattle 3G5 U.C.D. monoclonal antibody is coated onto colored latex particles in conventional manner. The same monoclonal antibody, or the rabbit polyclonal anti-bovine neutrophil antibody is coated in the form of a transverse strip onto a solid-phase member such as a piece of nitrocellulose or nylon membrane. The neutrophil antigen is sufficiently abundant in mastitic milk such that an antigen-antibody "capture" sandwich forms between the monoclonal antibody coloured particles and the solid-phase antibody to form a clearly visible coloured bar. No visible bar is seen if the neutrophil antigen is absent or at a low level. By using multiple strips or bars a semi-quantitative assay is possible. The solid phase member contains a well or application site for receiving a milk sample. The well or site may contain an amount of a lysing agent or, alternatively, the lysing agent is present in a "burst" blister or sachet adjacent the well and adapted to flow thereinto as required at the time of use.

What we claim is:

1. Method for detecting or determining mastitis or sub-clinical mastitis in an animal comprising capturing neutrophils or neutrophil fragments or soluble products thereof in a milk sample from said animal wherein said capturing is with an insolubilized antibody which specifically binds to neutrophils, neutrophil fragments or soluble fragments thereof but does not bind to any other type of cell, fragments of any other type of cell or soluble products thereof found in milk, determining the level of captured neutrophils, neutrophil fragments or soluble products thereof and comparing the level of captured neutrophils, neutrophil fragments or soluble products thereof in said sample to a level of captured neutrophils, neutrophil fragments or soluble products thereof in normal milk wherein an increased level in said sample is indicative of mastitis or sub-clinical mastitis in said animal.

2. Method of claim 1 wherein said insolubilized antibody is a monoclonal antibody which specifically binds to a heat labile, neutrophil specific protein containing material which has a molecular weight of from 10,000 to 20,000 daltons.

3. Method of claim 1, further comprising lysing cells in said milk sample and capturing with said insolubilized antibody, neutrophil fragments or soluble products thereof resulting from said lysing.

4. Method of claim 3, comprising lysing the cells of the milk sample by first freezing the milk sample and then thawing said milk sample.

5. Method of claim 3, comprising lysing the cells of the milk sample by treating said milk sample with a lysing agent.

6. Method of claim 3, comprising lysing the cells of the milk sample by treating said milk sample with a lysing agent selected from the group consisting of (i) complement and complement fixing antibody, (ii) a dissociating agent, (iii) a proteolytic enzyme, (iv) a salt at a concentration sufficient to lyse said cells, and (v) a surfactant.

7. Method of claim 3, comprising lysing the cells of the milk sample with a surfactant selected from the group consisting of an anionic, a cationic and a nonionic surfactant.

8. Method of claim 3, comprising lysing the cells of the milk sample with a surfactant selected from the group consisting of a polyoxyethylene ester of fatty acid, a polyoxyethylene sorbitan ester, a polyoxyethylene alcohol, a polyoxyethylene isoalcohol, a polyoxyethylene ester, a polyoxyethylene-p-t-octylphenol or octylphenyl-ethylene oxide condensate, an ethylene oxide condensate with a fatty alcohol, a polyoxyethylene nonylphenol, sodium N-lauroylsarcosinate, sodium dodecyl N-sarcosinate, sodium dodecyl sulphate, cetyltrimethylammonium bromide, dodecyl pyridinium chloride, palmitoyl lysolecithin, dodecyl-N-betaine, sodium dodecyl solphate, tetradecyl ammonium bromide, saponin and mixtures thereof.

9. Method of claim 3, comprising lysing the cells of the milk sample with a lysing agent which is a dissociating agent selected from the group consisting of potassium thiocyanate, sodium thiocyanate, guanidine thiocyanate, guanidine hydrochloride, potassium iodide, sodium iodide, potassium bromide, sodium bromide, ammonium chloride, ammonium sulphate, urea and mixtures thereof.

10. Method of claim 3, comprising lysing the cells of the milk sample with a lysing agent comprising a combination of a surfactant and a dissociating agent.

* * * * *

UNITED STATES PATENT AND TRADEMARK OFFICE
CERTIFICATE OF CORRECTION

PATENT NO.   : 5,168,044
DATED        : December 1, 1992
INVENTOR(S)  : Patrick J. Joyce It is certified that error appears in the above-identified patent and that said Letters Patent is hereby corrected as shown below:

Title page, [57] Abstract:
  Line 2:  Change "chemical" to -- clinical --.

Column 4, line 3:  change "wing" to -- using --.

Column 10, line 15:  change "0.150" to -- 0.140 --.

Column 13, Table 4:  in the table corresponding to "16" and in the column corresponding to "22", cross referenced to "Week 5", change "401 neg" and "423 neg" to -- 401 neg^ -- and -- 423 neg^ --.

Column 13, line 17, under "KEY TO TABLE 4", change "=" to -- ^= --.

Signed and Sealed this

Twenty-second Day of February, 1994

Attest:

BRUCE LEHMAN

*Attesting Officer*       *Commissioner of Patents and Trademarks*